United States Patent

Macchio et al.

[11] Patent Number: 6,045,783
[45] Date of Patent: Apr. 4, 2000

[54] COSMETIC FORMULATION WITH A SWELLING EFFECT

[75] Inventors: Ralph Macchio, Flanders, N.J.; Salvatore Barone, Staten Island, N.Y.; Celia Mohr, Somerset, N.J.; Alberto Guerrero, Orangeburg, N.Y.

[73] Assignee: Coty B.V., Haarlem, Netherlands

[21] Appl. No.: 09/309,254

[22] Filed: May 10, 1999

Related U.S. Application Data

[60] Provisional application No. 60/086,419, May 22, 1998.

[51] Int. Cl.⁷ .................................................. A61K 7/027
[52] U.S. Cl. ................................ 424/64; 424/63; 424/69; 424/401; 514/772.6
[58] Field of Search ................................ 424/401, 64, 63, 424/69; 514/772.6

[56] References Cited

U.S. PATENT DOCUMENTS

| | | | |
|---|---|---|---|
| 3,220,960 | 11/1965 | Wichterle et al. | 260/2.5 |
| 3,574,822 | 4/1971 | Shepherd et al. . | |
| 3,681,089 | 8/1972 | Gould et al. | 99/140 |
| 3,927,203 | 12/1975 | Seymour et al. . | |
| 3,963,685 | 6/1976 | Abrahams | 526/230 |
| 5,204,092 | 4/1993 | Mahieu et al. | 424/70 |
| 5,306,498 | 4/1994 | Vesperini et al. | 424/401 |
| 5,505,937 | 4/1996 | Castrogiovanni et al. | 424/64 |
| 5,616,598 | 4/1997 | Lion et al. | 514/374 |
| 5,637,291 | 6/1997 | Bara et al. | 424/59 |
| 5,660,839 | 8/1997 | Allec et al. | 424/401 |
| 5,700,453 | 12/1997 | Sato | 424/64 |
| 5,776,497 | 7/1998 | Lagrange et al. | 424/489 |
| 5,843,407 | 12/1998 | El-Nokaly et al. | 424/64 |
| 5,853,712 | 12/1998 | Langlois | 424/78.03 |
| 5,855,876 | 1/1999 | Deckner et al. | 424/64 |
| 5,874,069 | 2/1999 | Mendolia et al. | 424/65 |

FOREIGN PATENT DOCUMENTS

| | | |
|---|---|---|
| 195575 | 3/1986 | European Pat. Off. . |
| 0 356 196 A2 | 8/1989 | European Pat. Off. ......... A61K 7/48 |
| 0 487 000 A1 | 11/1991 | European Pat. Off. ......... A61K 7/48 |
| 3-246214 | 11/1991 | Japan . |

*Primary Examiner*—Thurman K. Page
*Assistant Examiner*—Patricia McGueeney
*Attorney, Agent, or Firm*—Collard & Roe, P.C.

[57] ABSTRACT

A cosmetic formulation with a swelling or volumizing effect, for use especially as a lipstick or other type of cosmetic, comprising:

a) a sodium polyacrylate polymer that swells numerous times beyond its original volume upon contact with moisture or water;

b) an emollient comprising cosmetically-acceptable oils, esters, liquid silicones and their mixtures within a range of 0.1–95 percent;

c) a wax comprising carnauba wax, candelilla wax, ozocerite, ceresin, paraffin, synthetic wax, bees wax, montan wax and mixtures thereof within a range of 0.1–50 weight percent;

d) an oil comprising castor oil, lanolin oil, synthetic oil, silicone oil and mixtures thereof within a range of 0.5–90 weight percent; and e) additional agents and adjuvants such as antioxidants, fats, fatty acid esters, lanolin, lanolin derivatives, dyes, pigments, perfume, protective agents, mica, talcum, silicon dioxide and synthetic resins that comprise a remaining portion of up to 100 weight percent.

17 Claims, No Drawings

COSMETIC FORMULATION WITH A SWELLING EFFECT

This application is based on Provisional Application Serial No. 60/086,419. filed on May 22, 1998.

FIELD OF THE INVENTION

The invention concerns a cosmetic formulation with a changeable volume.

For various cosmetic applications, e.g. make-up, it is desirable to have certain parts of the skin to appear fuller, especially the face. Normally, this is accomplished by special, thick-appearing pastes, especially make-up, multiple applications, semi-surgical or surgical measures, the injection of certain liquids, etc. All of these measures have the disadvantage that they can create problems for the skin of the user, or their structure does not retain the desired shape over long periods.

SUMMARY OF THE INVENTION

The invention is based on the problem of developing a lasting cosmetic formulation that is acceptable and effective for the skin, especially facial skin, and that increases in volume.

A special problem of the invention is to present a lipstick that increases in volume.

According to the invention, the cosmetic formulation with a swelling effect or volume-up effect comprises
a) a sodium polyacrylate polymer that swells numerous times beyond its original volume upon contact with moisture or water,
b) an emollient comprising cosmetically-acceptable oils, esters, liquid silicones and their mixtures within a range of 0.1–95 weight percent;
c) a wax comprising carnauba wax, candelilla wax, ozocerite, ceresin, paraffin, synthetic wax, bees wax, montan wax and mixtures thereof within a range of 0.1–50 weight percent;
d) an oil comprising castor oil, lanolin oil, synthetic oil, silicone oil and mixtures thereof within a range of 0.5–90 weight percent;
e) additional agents and adjuvants such as antioxidants, fats, fatty acid esters, lanolin, lanolin derivatives, dyes, pigments, perfume, protective agents, mica, talcum, silicon dioxide, synthetic resins, and polymers that comprise a remaining portion of up to 100 weight percent, beeing all free of water;
whereby the percentages refer to the overall formulation, and whereby the formulation contains less than 0.1 weight percent water.

The polyacrylate polymer is advantageously a poly (sodium acrylate) homopolymer or a sodium salt of polyacrylic acid or a mixture thereof. The particle size is preferably under 200 µm.

A particularly preferred complex for use in the formulation according to the invention is a separately-prepared mixture of polyacrylate polymers, e.g. sodium polyacrylate, an oil such as castor oil, and a solid antioxidant such as tocopheryl acetate. The portion of antioxidant is 0.5–2 weight percent, and the portion of the other two components is approximately the same.

In one embodiment of the invention, the portion of polyacrylate polymer can range from 0.1–60 weight percent; in another embodiment, it can range from 0.1–40 weight percent or 0.1–20 weight percent in reference to the overall amount of the cosmetic formulation.

A particularly preferred embodiment of the invention contains a polyacrylate polymer at an amount that allows the volume of the overall formulation to expand up to 150% of the original volume upon contact with moisture or water.

The formulation contains preferably less than 0.01% by weight water.

The cosmetically-acceptable oils, esters, and liquid silicones used in the formulation as an emollient or softener preferably comprise isoeicosane, dimethicone, myristyl myristate and behenyl erucate, whereby other materials such as vegetable oils can be used to the extent that they not produce any disadvantageous effects within the entire system. The amount of emollients is advantageously 1–60 weight percent and preferably 2–50 weight percent.

As stated, the formulation can contain other agents and adjuvants which, among other things, can be alcohols, polyols, stearic acid, magnesium stearate, cetearyl octanoate, corn starch and organic light stabilizers.

Among the oil-soluble UVB filters that can be used as light stabilizers are e.g. 4-aminobenzoic acid derivatives like 4-(dimethylamino)-benzoic acid-(2-ethylhexyl) ester, esters of cinnamic acid such as 4-methoxycinnamic acid-(2-ethylhexyl) ester, benzophenone derivatives like 2-hydroxy-4-methoxybenzophenone; 3-benzylidene camphor derivatives like 3-benzylidene camphor.

Pigments, pigment mixtures or powders with a pigment-like effect (which includes those with a pearly luster) can e.g. comprise iron oxide, titanium oxide ($TiO_2$), mica, kaolin, talcum, mica-titanium oxide, mica-titanium oxide/iron oxide, bismuth oxychloride, nylon spheres, ceramic spheres, expanded and non-expanded synthetic polymer powders, powdered natural organic compounds such as ground solid algaes, encapsulated and unencapsulated grain starches, as well as mica-titanium oxide organic dyes, $ZrO_2$, MnO, $Al_2O_3$, etc. can be used.

The formulation according to the invention is in the form of a lipstick, foundation, mascara, make-up, concealer, etc.

We know that the polyacrylates used according to the invention can be used in hygienic products such as diapers and sanitary napkins, etc. as an absorbent material. Their use in cosmetics is new and requires the solution to a series of problems such as adjusting the system so that no precipitation or agglomeration occurs, and working without the presence water. It was surprisingly found that a stable cosmetic formulation can be obtained with a mixture of emollients, waxes, oils and selected additional agents and adjuvants. The formulation can be processed into sticks such as lipsticks when the wax content is high, or pasty formulations when the wax content is very low.

One special embodiment of the invention concerns a lipstick with a wax component of 8–15 weight percent, an oil component of 22–32 weight percent, a component of polyacrylate polymers of 4–12 weight percent, a component of emollients of 2–20 weight percent, with the remaining component being other agents and adjuvants.

Another subject of the invention is a procedure to prepare a cosmetic formulation with a swelling effect wherein a first homogenous mixture is prepared of a polyacrylate polymer, an oil such as castor oil, and a solid antioxidant by mixing the individual components at $\leq 50°$ C., and after that a second mixture is prepared by mixing the first mixture at $\leq 50°$ C. with the other components without the presence of water. Preferred mixing temperatures are 20–50° C. resp. 30–50° C. for preparing the first resp. the second mixture. The expert will understand that specific, previously-determined individual phases of the formulation are prepared and then included in the mixture with the above complex of polymer/oil/antioxidant which is the first mixture.

In addition to the swelling or volume-up of the formulation according to the invention, its other great advantages are longevity (long lasting effect), a smoothing effect, and the fact that individual components do not bleed, and also its excellent skin compatibility. For the first time in cosmetics, the mouth can be accented not only by applying coloured lipsticks, but also by making the lips appear fuller.

Also other parts of the body can be accented by applying the new formulation and optionally adding humidity.

User tests of lipsticks have shown a clear acceptance. The feel on the lips after application is pleasant and smooth, and one feels that the lips appear to have a greater volume. The contours last, and the evaluation of the lip feel is mostly good or very good even after the lipstick has been worn for a long while.

DETAILED DESCRIPTION OF PREFERRED EMBODIMENT

The invention will be further explained in the following with reference to examples. All figures are in weight percent unless otherwise indicated.

EXAMPLE 1

Lipstick

| Phase A | |
|---|---|
| Carnauba Wax | 2 |
| Candelilla Wax | 6.5 |
| Ozocerite | 3 |
| Behenyl Erucate | 2.5 |
| Myristyl Myristate | 3 |
| Oleyl alcohol | 11 |
| Lanolin | 8 |
| Polydecene | 9.5 |
| Ca-Al-B Silicate | 2.5 |
| Phase B | |
| Castor Oil | ad 100 |
| Phase C | |
| Dyes | 8 |
| Castor Oil + Tocopheryl Acetate | 11 |
| Phase D | |
| Mica | 2 |
| Phase E | |
| Sodium Polyacrylate | 7 |
| Castor Oil | 7 |
| Tocopheryl Acetate | 1 |
| Phase F | |
| Fragrance | 1 |

The components of phase A were mixed in a vat at approx. 85–95° C. While holding the temperature at this level, the components of phase B were added and mixed until they were evenly distributed. After adding phase C at 80°–85° C. under continued mixing, phase D was added at this temperature, and the mixing was continued for one hour while maintaining the temperature.

By mixing the individual components of phase E, a dispersion was created with a viscosity of 7500–8500 cps. After sufficient dispersion at ≦50° C., phase E was added to the above described mixture of phases A–D also at ≦50° C. Then after mixing briefly for approximately 1 min., phase F was added. Subsequently the finished mixture was poured into corresponding molds and cooled.

The following products were prepared like this way.

EXAMPLE 2

Lipstick

| Carnauba Wax | 2.5 |
|---|---|
| Candelilla Wax | 3.5 |
| Ozocerite | 7 |
| Behenyl Erucate | 2 |
| Caprylic/Capric Triglyceride | 9 |
| Polydecene | 6.5 |
| Lauryl Lysine | 2.5 |
| Castor Oil | ad 100 |
| Colours | 10.5 |
| Mica | 5 |
| Sodium Polyacrylate | 5 |
| Tocopherol Acetate | 2 |
| Fragrance | 1 |

EXAMPLE 3

Cream Foundation

| Carnauba Wax | 4.5 |
|---|---|
| Tridecyl Trimellitate | 11.5 |
| Sodium Polyacrylate | 6 |
| Castor Oil | 6 |
| Butylparaben | 0,06 |
| Cetyaryl Octanoate | ad 100 |
| Magnesium Stearate | 3 |
| Polymethyl Methacrylate | 10 |
| Corn Starch | 3 |
| Colours | 4.5 |
| Mica | 21 |
| Talc | 18 |
| Silica | 2 |

EXAMPLE 4

Mascara

| Stearic Acid | 9 |
|---|---|
| Montan Wax | 1.5 |
| Beeswax | 8.5 |
| Isopropyl Lanolate | 3.5 |
| Sodium Polyacrylate | 4 |
| PVP/Eicosene Copolymer | 0.5 |
| Castor Oil | ad 100 |
| Glycerin | 2 |
| Hectorite | 0.3 |
| Acacia Catechu | 2 |
| Colours | 13 |
| Mica | 2 |
| Trisamino | 2 |
| Diazolidinyl Urea | 0.3 |
| Phenoxyethanol | 1 |
| Fragrance | 0.3 |
| Water | 0.05 |

PRACTICAL EXAMPLE

The following practical example was carried out in the form of an investigation (study) of a lipstick prepared according to example 1 (specimen 1) and a commercially-available comparative lipstick, "Rising Sun" (specimen 2) by Margaret Astor.

Modeled lips were made of a dental casting material to which the test specimen was applied. The image analyzer used for the investigation with special software works at an angle of 90° which allows a computer image of the lip model to be created. The thickness of the test material at the edge of the lips was measured by the image analyzer. The dark product colour on the lip model allows the computer to measure the product thickness by determining the colour contrast of the lip edge to the product.

After applying the lipstick to the model lips with a moisturized applicator (cotton swab) using a rolling movement over 15 seconds, the image analyzer was turned on after a waiting period of one minute. The moist applicator also simulated the normal licking of the lips that occurs after applying lipstick to natural lips.

The thickness of the specimen was measured after the activation time. Then the model lips were washed, and the lipstick was reapplied.

20 repeated measurements of the lipstick revealed an average product thickness of 196 $\mu$m for specimen 2 and 289 $\mu$m for specimen 1. This corresponds to a swelling of 48% for specimen 1. The statistical significance of the measurements was $P \leq 0.05$.

We claim:

1. A cosmetic formulation with a swelling effect, comprising:
   a) a substance comprising at least one of a Poly(sodium acrylate) homopolymer, and sodium salt of polyacrylic acid, which swells up to 5 times beyond its original volume upon contact with moisture, the amount of the substance being in a range of 0.01–90 weight percent;
   b) an emollient selected from the group consisting of cosmetically-acceptable oils, esters, liquid silicones and their mixtures within a range of 0.1–95 weight percent;
   c) a wax selected from the group consisting of carnauba wax, candelilla wax, ozocerite, ceresin, paraffin, synthetic wax, bees wax, montan wax and mixtures thereof within a range of 0.1–50 weight percent;
   d) an oil selected from the group consisting of castor oil, lanolin oil, synthetic oil, silicone oil and mixtures thereof within a range of 0.5–90 weight percent; and
   e) additional agents and adjuvants selected from the group consisting of antioxidants, fats, fatty acid esters, lanolin, lanolin derivatives, dyes, pigments, perfume, protective agents, mica, talcum, silicon dioxide, and synthetic resins, that comprise a remaining portion of up to 100 weight percent, wherein the percentages refer to the overall formulation, and wherein the formulation contains less than 0.1 weight percent water.

2. A formulation according to claim 1, wherein the cosmetically acceptable oils, esters, and liquid silicones used comprise isoeicosane, dimethicone, myristyl myristate and behenyl erucate.

3. A cosmetic formulation according to claim 1 for application on the facial skin or skin section, to increase the volume of the applied formulation after it contacts moisture or water.

4. A formulation according to claim 1, wherein it contains a poly(sodium acrylate) polymer at an amount that leads to the swelling of the overall formulation up to 150% of the original volume upon contacting moisture or water.

5. A formulation according to claim 1, wherein the amount of poly(sodium acrylate) polymer ranges from 0.1 to 60 weight percent.

6. A formulation according to claim 1, wherein the amount of poly(sodium acrylate) polymer ranges from 0.1 to 40 weight percent.

7. A formulation according to claim 1, wherein the amount of poly(sodium acrylate) polymer ranges from 0.1 to 20 weight percent.

8. A formulation according to claim 1, wherein the poly(sodium acrylate) polymer swells up to the 5-fold beyond its original volume upon contact with moisture or water.

9. A formulation according to claim 1, wherein the formulation is in the form of a lipstick, foundation, mascara, make-up, or concealer.

10. A formulation according to claim 1, wherein the formulation contains less than 0.01 weight percent water.

11. A formulation according to claim 1, wherein the formulation is in the form of a lipstick with a wax component of 8–15 weight percent, an oil component of 22–32 weight percent, a poly(sodiumacrylate) polymer component of 4–12 weight percent, an emollient component of 2–20 weight percent with the remainder being agents and adjuvants.

12. A formulation according to claim 11, wherein the formulation contains less than 0.01 weight percent water.

13. A formulation according to claim 1, wherein the amount of emollient is 1–60 weight percent.

14. A formulation according to claim 1, wherein the amount of emollient is 2–50 weight percent.

15. A procedure to prepare a cosmetic formulation with a swelling effect wherein a homogenous mixture is prepared consisting of polyacrylate polymer, castor oil and a solid antioxidant by mixing the individual components at $\leq 50°$ C., and this mixture is mixed at $\leq 50°$ C. with the emollient and wax, all without the presence of water.

16. A cosmetic formulation according to claim 1 for application on the skin, to increase the volume of the applied formulation after it contacts moisture or water.

17. A cosmetic formulation according to claim 1 for application to the lips to increase the volume of the applied formulation after it contacts moisture or water.

* * * * *